(12) United States Patent
Cargol et al.

(10) Patent No.: US 7,057,393 B2
(45) Date of Patent: Jun. 6, 2006

(54) SYSTEM AND METHOD FOR MEASURING THE DIELECTRIC STRENGTH OF A FLUID

(75) Inventors: Timothy L. Cargol, Somerville, MA (US); Chathan M. Cooke, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 122 days.

(21) Appl. No.: 10/007,876

(22) Filed: Dec. 6, 2001

(65) Prior Publication Data

US 2003/0067311 A1    Apr. 10, 2003

Related U.S. Application Data

(60) Provisional application No. 60/251,697, filed on Dec. 6, 2000.

(51) Int. Cl.
*G01N 27/02* (2006.01)
*G01R 27/26* (2006.01)

(52) U.S. Cl. .................. 324/444; 324/658; 324/663

(58) Field of Classification Search ............ 324/444, 324/425, 619, 658, 67, 668; 327/276, 283, 327/268, 552, 559
See application file for complete search history.

(56) References Cited

U.S. PATENT DOCUMENTS

| | | | | |
|---|---|---|---|---|
| 3,801,799 A * | 4/1974 | Atkins | ................. | 307/116 |
| 3,879,657 A | 4/1975 | Nystuen et al. | ................. | 324/30 |
| 3,944,917 A * | 3/1976 | Hogg et al. | ................. | 324/71.1 |
| 3,996,512 A | 12/1976 | Baur | ................. | 324/61 |
| 4,093,915 A * | 6/1978 | Briefer | ................. | 324/679 |
| 4,629,334 A * | 12/1986 | Hochstein | ................. | 374/103 |
| 4,646,070 A * | 2/1987 | Yasuhara et al. | ................. | 340/603 |
| 4,663,585 A | 5/1987 | Kruger et al. | ................. | 324/54 |
| 4,686,857 A | 8/1987 | Kato | ................. | 73/304 |
| 5,270,663 A * | 12/1993 | Sano et al. | ................. | 324/676 |
| 5,504,430 A * | 4/1996 | Andersson | ................. | 324/439 |
| 5,555,205 A * | 9/1996 | Okabe | ................. | 365/108 |
| 5,611,240 A * | 3/1997 | Yamaguchi | ................. | 73/304 C |
| 5,646,539 A * | 7/1997 | Codina et al. | ................. | 324/678 |
| 5,973,538 A * | 10/1999 | Shou et al. | ................. | 327/344 |

(Continued)

FOREIGN PATENT DOCUMENTS

GB    2 187 290    9/1987

OTHER PUBLICATIONS

"Progress in the field of electric breakdown in dielectric liquids," Sharbaugh et al. *IEEE Trans. Electr. Insul.* Aug. 1978. vol. EI-13, No. 4.

(Continued)

*Primary Examiner*—Anjan Deb
*Assistant Examiner*—John Teresinski
(74) *Attorney, Agent, or Firm*—Gauthier & Connors LLP

(57) ABSTRACT

A system is disclosed for monitoring the quality of an internal fluid contained in an apparatus. The system includes a pulse input port, a test gap unit, and a reactive impedance unit. The pulse input port receives a test pulse input signal from a pulse source. The test gap unit provides a test voltage across a test gap while the test gap unit is immersed in the internal fluid within the apparatus. The test gap unit has an inherent capacitance. The reactive impedance unit provides an impedance in series with the inherent capacitance of the test gap unit that restricts transfer of current to the test gap, and is coupled to the pulse input port and coupled to the test gap unit. The impedance unit includes a first resistor unit in parallel with a capacitor unit.

17 Claims, 2 Drawing Sheets

U.S. PATENT DOCUMENTS 6,664,793 B1 * 12/2003 Sampson et al. ........... 324/439

OTHER PUBLICATIONS

"Studies on the Dielectric Strength of Transformer Oil Under Oscillatory Impulse Voltages," Ventakataseshaiah et al. *IEEE International Symposium on Electrical Insulation.* Jun. 1996.

Database WPI, Section EI. Week 198427. Derwent Publications Ltd., London, GB. Oct. 1983.

* cited by examiner

SYSTEM AND METHOD FOR MEASURING THE DIELECTRIC STRENGTH OF A FLUID

This application claims priority to U.S. Provisional Patent Application Ser. No. 60/251,697 filed Dec. 6, 2000.

BACKGROUND OF THE INVENTION

The present invention generally relates to the field of electric power transformer systems, and particularly relates to such systems that use an internal fluid, such as oil, for dielectric and/or heat transfer purposes.

Oil is used extensively as an internal fluid in modern electric power apparatus, for example in power transformers of most transmission systems. Oil generally serves two necessary functions; to insulate voltage between metallic conductors at close clearances, and to aid in the removal of heat generated by losses in the conductors. Unfortunately, oil can degrade and loose it's ability to adequately insulate voltage and thereby enhance the risk of a dielectric failure; this in-turn can lead to a forced outage and/or catastrophic failure. The direct dollar cost of a single failure may be very expensive (possibly exceeding ten million dollars) and may further cause adverse implications for safety and the environment.

It is known to employ regular inspection of transformer oil condition, often on an annual basis and especially in oil insulated tap changer compartments. Such inspections typically involve careful manual extraction of an oil sample and subsequent testing in a dielectric strength tester. The dielectric strength test is typically made in accordance with a recognized standard procedure and apparatus, typically via standards such as the American Society of Testing Materials (ASTM) D-877 or D-1816 or certain international standards such as provided by IEC/VDE authorities. Such tests apply an AC voltage stress to an electrode pair immersed in the subject oil, the stress is continuously increased until breakdown occurs. The voltage at breakdown is the measure of insulating ability. These standard tests employ defined electrodes, defined applied AC high voltage at fixed rates of rise until breakdown, and a statistical method for interpreting the results of a few repeated tests.

Unfortunately such conventional test must be performed on a sample because they are destructive to the oil. The sample measured is discarded after the test. This means that the test cannot be used on oil directly inside an operating power apparatus. The oil must be extracted so as not to compromise the integrity of the operating unit. The costs and limitations imposed by manual sampling and measurement require that dielectric strength tests are performed typically on an annual or semiannual basis. This may permit more rapid degradation to be undetected in some cases, resulting in occasional failures.

In an attempt to achieve in-service measurement, two techniques have been employed. One uses an active detection and fast switch device to detect the onset of a discharge and to rapidly interrupt or divert the supply source. This is limited in effectiveness because of the necessity for reliable and very fast interruption of high-voltages, a difficult task. A failure of any of the interruption mechanism would result in degradation of the oil and possible faulting of the power apparatus being tested.

A second technique, referred to as the Non-Destructive Breakdown method, NDBD, employs a pulsed high-voltage applied to electrodes in an oil test gap. The gap is selected such that there is no breakdown event for the NDBD pulse voltage for good oil condition; however as the oil condition degrades then NDBD applied voltage induces breakdown events. The oil condition is assessed from the NDBD breakdown activity. Three major differences that distinguish the NDBD measurement from the ASTM—type dielectric strength tests are (1) it uses time-lag to breakdown at pulse voltage, instead of a 60 Hz AC voltage raised to BD, (2) it uses a short (submicrosecond) duration constant pulse voltage from a pulser; and (3) it use a negative point-to-plane electrode, instead of ASTM symmetric planar electrodes.

To reduce the effects of statistical variations inherent in the breakdown process, the ASTM test specifies repeated measurements under fixed conditions to more clearly distinguish degradation. Because of changes to the oil due to damage induced by the breakdowns in the test itself however, there is typically a limit of 5 breakdowns maximum on any oil sample. In contrast, the NDBD test allows many more repeated measurements and thus greater accuracy of the measurement.

It is important to recognize that in the NDBD approach the test induces no breakdown events in clean (or good) oil and hence no damage to the oil is possible when the oil is clean. However, when the oil does degrade, detection is achieved by the onset of breakdown activity of the NDBD test events. The occurrence of repeated breakdowns is one signature of a degraded oil condition. Hence it is an essential part of the oil condition assessment that the NDBD test will exhibit progressively greater probability of breakdown in any series of tests as the oil condition significantly degrades. The NDBD test breakdowns must, therefore, not themselves be the cause of significant degradation to the oil, especially for the NDBD test to be acceptable as a measurement performed on oil inside a power apparatus, without oil extraction.

Although conventional NDBD tests on samples yield improvements in reduced oil degradation compared to the ASTM-type tests, the NDBD tests are not suitable for in-service testing, i.e., during operation of the electric power apparatus. The difficultly with performing in-service tests, is that some degradation of the oil may result from the testing itself. Such damage is related to the currents in the oil during breakdown. The characteristic surge impedance of the pulser voltage acts to provide an inherent limit to the current and thereby possible damage to the oil under test. For example, for a 20 kV pulse voltage and a 50 ohm line impedance, a current limit of 400 amperes is achieved for the very short duration of the pulse, e.g., up to 0.3 microseconds. The charge transfer could therefore attain a value of about 120 microcoulombs for this case. The integral of current squared times time is another measure used to quantify the activity of a discharge and for this case amounts to about $5 \times 10^{-2}$ $amps^2$-seconds. These values are typically ten times or more smaller than breakdown events from a classical ASTM type test, but still provide conditions in which damage to the oil may result.

There remains a need, therefore, for a system and method for achieving in-service measurement of the dielectric strength of oil in an electric power apparatus.

SUMMARY OF THE INVENTION

The invention provides a system for monitoring the quality of an internal fluid contained in an apparatus. In accordance with an embodiment, the system includes a pulse input port, a test gap unit, and a reactive impedance unit. The pulse input port receives a test pulse input signal from a pulse source. The test gap unit provides a test voltage across a test gap while the test gap unit is immersed in the internal fluid within the apparatus. The test gap unit has an inherent capacitance. The reactive impedance unit provides an impedance in series with the inherent capacitance of the test gap unit that restricts transfer of current to the test gap, and is coupled to the pulse input port and coupled to the test gap unit. The impedance unit includes a first resistor unit in parallel with a capacitor unit.

BRIEF DESCRIPTION OF THE DRAWINGS

The following description may be further understood with reference to the accompanying drawings in which.

The drawings are shown for illustrative purposes.

DETAILED DESCRIPTION OF THE INVENTION

The invention provides a system and method for measuring oil dielectric strength within a power apparatus. This disclosed apparatus improves the NDBD test so as to be suitable for use directly in a power apparatus without oil extraction and hence may be performed in-service, i.e., while the apparatus is energized in-service.

The invention provides that the need for and cost of manual oil extraction for dielectric strength evaluation may be eliminated, and enables early detection of oil degradation by more frequent and automated dielectric strength tests. The operation of the test in accordance with the invention may be performed selectively on-site, and may even be automated if desired. An automated system for performing such in-service tests enables the opportunity for remote control and access to the test so that manual activity at the site for such oil condition tests is eliminated. The in-service tests enabled by the disclosed apparatus thus will reduce costs and improve early warning detection and thereby allow maintenance based on need with reduced risk of oil induced failure. The avoidance of manual oil extraction also reduces the risk of oil spills and other possible environmental hazards.

In an embodiment, a system of the invention provides a special apparatus that enhances the usefulness of the NDBD type oil dielectric strength test. The basic NDBD test method acts to greatly reduce the energy delivered and the amount of damage to the oil compared to traditional tests. However, substantial further improvements to the NDBD test performance and reduced discharge effects on the oil have been demonstrated and achieved with a system of the invention as disclosed below.

Figure 1:
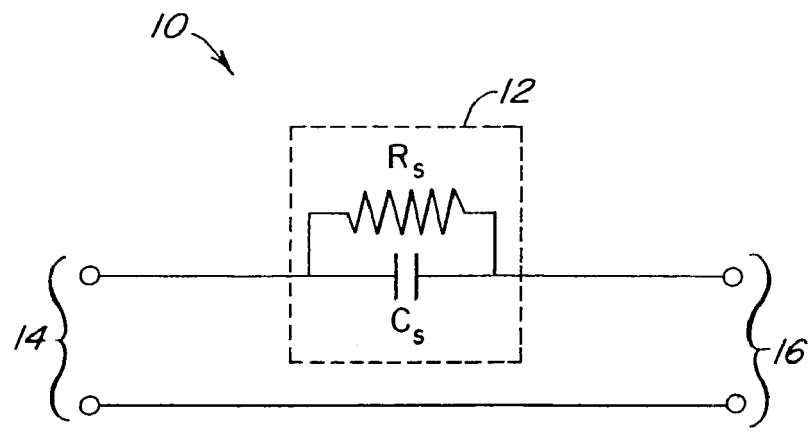
FIG. 1 shows an illustrative view of a circuit in accordance with an embodiment of the invention.

As shown in FIG. 1, a system 10 of the invention includes a series impedance 12 that is coupled between a pulse input port 14 and a gap device port 16. The series impedance 12 is added to directly control the pulse currents in the test gap so as to reduce the impact of the NDBD test on the oil and thereby make the test more suitable for in-service application, while at the same time permitting reliable breakdown measurements. Specifically, it has been found that the test reliability and performance of the point to plane gap, which is driven by a pulse voltage in the NDBD test method, is greatly improved by an added series impedance which acts to further control the pulse currents during an NDBD test event. The effect of the added series impedance is to cause the NDBD discharge events to be micro-discharge events with greatly reduced energy deposited into the oil and reduced wear of the point test electrode tip.

Measurements indicate that the significant reductions in the effects on the oil are achieved when the series impedance causes additional limiting of the steady current that flows through the test gap after breakdown. Further, the selected series impedance provides the beneficial effect of providing a very short duration pulse of current, which has been found to produce a self-induced oil flow that can act to aid in the clearing of debris from the active gap region. These findings support the experimental observation that a series impedance incorporating a capacitance greatly improves the NDBD test. This series capacitance may also have a resistance that ensures the capacitance can discharge between tests. Because the NDBD test requires a high voltage at the test electrodes, the added series impedance 12 must be carefully chosen to allow the needed test voltage to appear across the test electrodes, but not interfere with operation.

Figure 2:
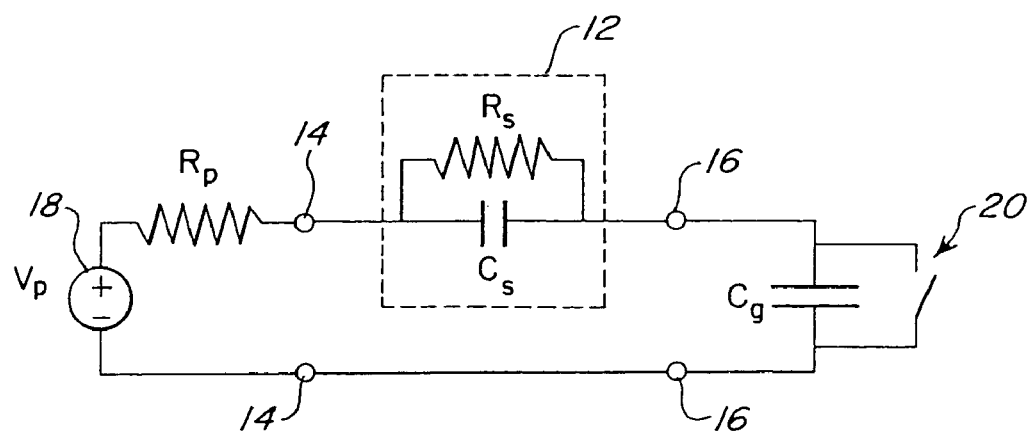
FIG. 2 shows an illustrative view of the circuit of FIG. 1 in a test system that is coupled to an electrical power apparatus in accordance with an embodiment of the invention.

It is important to significantly reduce any impact of the NDBD test on the oil. The added series impedance is introduced intentionally to greatly reduce the total amount of current that is available at the test gap from the pulser, typically by factors of 10 or more. A preferred embodiment for this series impedance is a high-voltage capacitor, $C_S$, in parallel with a high-voltage resistor, $R_S$, as shown in FIG. 1. The resistance, $R_S$, preferably of more than 10 kilohms and less than 10 megohms is used to dissipate any residual charge or voltage accumulated on the series capacitor after a test event. During operation, this series impedance is in series with the output of a pulser 18, and pulser 18 has an inherent resistance $R_P$ that is shown diagrammatically in FIG. 2. The test gap equivalent circuit is also shown in FIG. 2, and includes an inherent capacitance $C_g$ that is in parallel with a switch 20. The switch 20 represents the spark event when it closes. The series impedance may be physically located on either the 'high-side' as depicted in the figure or on the 'return-ground lead' side of the test gap with essentially the same effect, except for possible small differences due to the effects of stray capacitances.

Typically, the added capacitance of the example series impedance, $C_S$, is selected to be large compared to the effective series capacitance of the test gap itself so that most of the pulse voltage appears across the test gap. It is also selected to be small to restrict the currents through the test gap. Examples include a 100 pF added series capacitance, $C_S$, for a test gap capacitance, $C_g$, of 10 pF. These two capacitors in series form a capacitive voltage divider, and with these illustrative values essentially 90% of the pulser voltage is still applied to the test gap. $R_S$ is much greater than the pulser source resistance $R_P$ so as to influence the steady current after breakdown.

To understand the operation with this added series impedance consider three modes for this equivalent circuit. The first is where the pulser $V_P$ is on, and there is no breakdown at the test gap, so the gap-switch 20 is open. The circuit charges with a time constant of essentially $R_P C_g$ since $C_g$ is in series with $C_S$ and $C_S$ is greater than $C_g$. At the above values the time constant is 5 ns, neglecting stray capacitances that may increase the time. After several time charging constants, the voltage on the test gap equalizes at about 90% of the pulser voltage, according to the capacitor divider action of $C_g$ and $C_S$.

In the condition where the pulser is on and breakdown occurs, the gap-switch 20 is closed. The charge on the gap capacitance $C_g$ is dissipated in the closed switch 20 and the gap voltage becomes very small. Now current from the pulser is fed into the closed test gap via the added series circuit. At first, the series capacitance $C_S$ acts as a short and the current in the test gap is limited by the pulser effective impedance $R_P$, $I_{PK}=V_P/R_P=400$ amps for the illustration values. The added series capacitance then charges with a time constant of approximately $R_PC_S$, about 50 ns in the example case. As the capacitance $C_S$ changes, the current in the test gap decreases. A small steady gap current is then sustained by the high value series resistance $R_S$ with an equilibrium value of about $V_P/R_S$, about 0.1 amp. This is a 4000 times reduction from the 400 amp level without the added series impedance.

With this added series impedance the voltage at the pulser output may remain high during this time after breakdown, but the voltage on the test gap can be small because of the series voltage drop across the added series impedance. For larger series resistance, $R_S$, the current during breakdown may be reduced further below the 0.1 amp level, but no further significant change in the oil occurs because the effect is already reduced below that which may be caused during the gap closing.

In the third condition, the pulser is off, and there is no breakdown. Here the circuit is decaying to rest so that all currents and voltages in this circuit tend toward zero. This process typically takes on the order of seconds or minutes, so the above time constants are more than fast enough to ensure that the circuit is at rest before the next pulse test.

With the illustrative values mentioned above for the series circuit elements, the net effect on the discharge was measured and shown to reduce the energy delivered to the oil gap by more than ten times compared to without the series impedance. A further experimental indicator of improvement achieved by the added series impedance was a major reduction of micro-bubbles in the oil observed after a microbreakdown discharge with series impedance versus those after a discharge without the series impedance.

There are two additional features that make the above embodiment of a series circuit simple yet very effective. The above specific added series impedance exhibits two different and favorable time constants. In the first mode above, the gap is open without breakdown and the effective resistance seen by the capacitance $C_S$ is essentially $R_S$. There is, therefore, a long time constant for the capacitor and most of the pulser voltage remains across the test gap throughout the 300 ns long test pulse duration. In contrast, after breakdown in the second mode, the effective resistance seen by the capacitor is now $R_P$, which is a smaller value than $R_S$. This means that the response will have a short time constant, and the same capacitor becomes very effective in limiting the current in the test gap even within the test duration of 300 ns.

Figure 3:
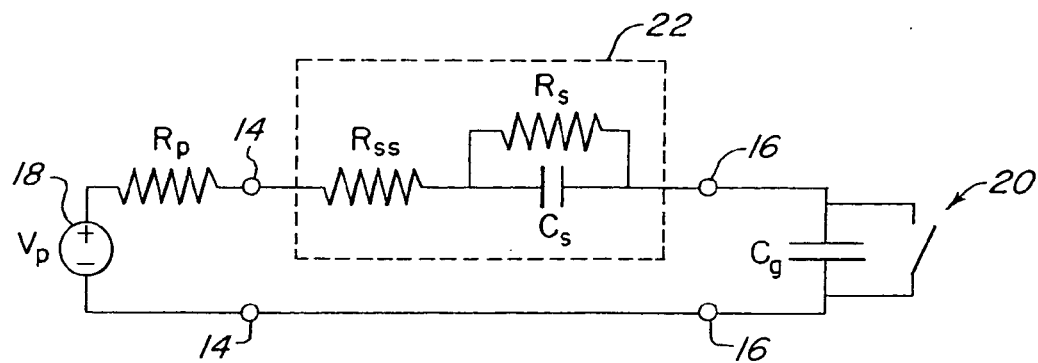
FIG. 3 shows an illustrative view of a circuit in accordance with a further embodiment of the invention.

In another embodiment of the invention as shown in FIG. 3, a second series resistance $R_{SS}$ (22) of the pulser is set to be a moderate value, such as 500 ohms. This value is much greater than the raw 50 ohm impedance used at first and is tolerated because the resultant time-constant remains suitable for a typical test pulse of 300 ns duration. Greater than 50 ohms is desirable because it is a simple way to limit the current during the initial time just after breakdown. This higher resistance may be obtained in practice for example, by creating a high impedance transmission line pulser or using a typical 50 ohm pulser and adding a series output resistance to attain an approximately 500 ohm value. The pulser effective series impedance may need to be adjusted to allow for the charge and discharge features discussed above associated with the pulse duration and gap capacitance.

As further shown in FIG. 3, the series impedance 22 is coupled between a pulse input port 14 and a gap device port 16. The series impedance 22 includes a series capacitor $C_S$ and a series resistor $R_S$ as discussed above with reference to FIGS. 1 and 2, and further includes a second series resistor, $R_{SS}$, on either side of the $R_SC_S$ pair. The value of $R_P$ is the inherent pulser source impedance, perhaps associated with the surge impedance of a transmission-line type pulser; here typical values might be 50 or 75 ohms due to the surge impedance of many practical coaxial cables. The added series resistor $R_{SS}$ is introduced to further limit the current to the test gap. This resistance is chosen to limit the peak current available to the test gap and still allow sufficiently rapid charging of the test voltage within the duration of the test voltage. For example $R_{SS}$ might be about 500 ohms for a test pulse width of 300 ns and a gap capacitance of about 10 pF, and $R_P$ of 50 ohms.

The capacitance $C_S$ also serves the purpose of creating a short pulse of current. This current has been found to be linked to a pulsive oil flow circulation at the gap when the pulse is applied and thereby helps keep the test gap clear of debris. The exact cause as to how the action by the electrical pulse is linked to the oil flow is not fully understood, but example mechanisms may be the magnetic repulsive force associated with the pulsed current or charge carrier motion. While the use of a capacitor produces a pulse of current, beneficial for oil flow clearing, the selection of a suitably short time constant allows this pulse current to subside rapidly so as to limit possible subsequent damage to the oil. Note that the values of the series impedance and the pulser effective source impedance are chosen together to create an overall control of the NDBD pulse supplied to the test gap, including rise and fall times, peak currents and steady currents as well as voltages.

Figure 4A:
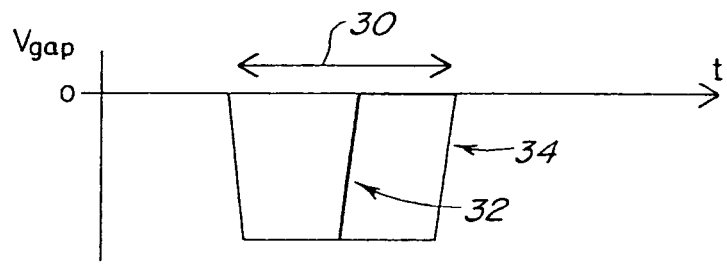
FIG. 4A shows an illustrative graphical view of gap voltage ($V_{gap}$) versus time for a test system in accordance an embodiment of the invention.
Figure 4B:
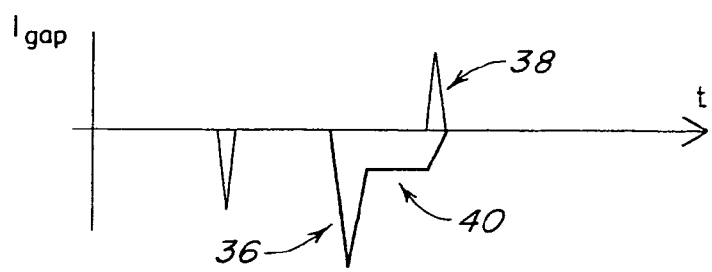
FIG. 4b shows an illustrative graphical view of gap current ($I_{gap}$) versus time for a test system in accordance an embodiment of the invention.

The series impedance of this invention may be comprised of single lumped elements, or may include distributed elements that cause equivalent current control. An illustration of the overall resultant voltages and currents associated with the test gap for the disclosed invention is depicted in FIGS. 4A and 4B. As shown in FIG. 4A, an applied pulse width (of for example 300 ns) is shown at 30, and the voltage with breakdown is shown at 32 while the voltage without breakdown is shown at 34. The current at the gap over time for the pulse 30 is shown in FIG. 4B, and the current with breakdown is shown at 36 while the current without breakdown is shown at 38. The reduced current with the added series impedance is shown at 40.

The selection of the series impedance may also be influenced by the circuit equivalent of the apparatus to which it is connected. For example, a smaller capacitance test gap, $C_g$ may allow the series capacitance, $C_S$, to be smaller and yet keep the same voltage ratio between pulser output and the voltage on the test gap. The use of standard classical circuit and transmission line analysis techniques may be used to establish the series impedance needed to achieve the desired current control. These calculations include factors such as capacitances and surge impedances.

The application of the disclosed invention is for any high-voltage diagnostic measurement where an essentially capacitive test gap is driven by a pulse voltage source.

Examples provided, which are illustrative but not limiting in scope, reveal that the basic circuit topology comprised of a pulser with effective output impedance may be connected to an essentially capacitive test gap via a series impedance selected to control currents in order to reduce damaging effects from the discharge by limiting the steady current while at the same time provide a short pulse of current and adequately fast voltage transitions.

In further embodiments, the methods and systems of the invention may be used to evaluate fluid degradation is other fluid containing apparatus, including gas turbines or internal combustion engines, or other machinery in which the degradation of a fluid may develop.

The system and method of this invention provide numerous benefits compared to systems and methods that involve a classical current limit approach that is imposed by a fixed surge impedance of the output characteristics from a typical transmission line pulser or other standard high-voltage pulser.

Those skilled in the art will appreciate that numerous modifications and variations may be made to the above disclosed embodiments without departing from the spirit and scope of the invention.

What is claimed is:

1. A system for monitoring the quality of an internal fluid contained in an apparatus, said system comprising:
    a pulse input port for receiving a test pulse input signal from a pulse source;
    a test gap means for providing a test voltage across a test gap while said test gap means is immersed in the internal fluid within the apparatus, said test gap means having an inherent capacitance; and
    reactive impedance means for providing an impedance in series with the inherent capacitance of said test gap means that restricts transfer of current to the test gap, said reactive impedance means being coupled to said pulse input port and coupled to said test gap means, and including a first resistor unit in parallel with a capacitor unit.

2. The system as claimed in claim 1, wherein said reactive impedance means includes a second resistor unit in series with said first resistor unit.

3. The system as claimed in claim 2, wherein said second resistor unit has a resistance value that is less than a resistance value of said first resistor unit.

4. The system as claimed in claim 1, wherein said reactive impedance means includes a second resistor unit in series with said capacitor unit.

5. The system as claimed in claim 1, wherein said reactive impedance means includes a second resistor unit in series with both said first resistor unit and said capacitor unit.

6. The system as claimed in claim 2, wherein said second resistor unit is selected to have a value that limits a peak current that is available at the test gap.

7. The system as claimed in claim 1, wherein said first resistor unit has a resistance value of between about 10 K Ohms and about 10 M Ohms.

8. The system as claimed in claim 1, wherein said capacitor unit has a capacitance value of about 100 pF.

9. A system for monitoring the quality of a fluid in a fluid insulated high voltage apparatus, said system comprising:
    a pulse input port for receiving a test pulse input signal from a pulse source;
    a test gap means for providing a test voltage across a test gap while said test gap means is immersed in the fluid within the high voltage apparatus, said test gap means having an inherent capacitance; and
    a current restrictive impedance unit for providing an impedance in series with the inherent capacitance of said test gap means, said impedance unit including a first resistor in parallel with a capacitor, and said impedance unit being coupled to said pulse input port and coupled to said test gap means.

10. A system as claimed in claim 9, where in said impedance unit further includes a second resistor in series with said first resistor.

11. The system as claimed in claim 10, wherein said second resistor is selected to have a value that limits a peak current that is available at the test gap.

12. The system as claimed in claim 9, wherein said impedance unit further includes a second resistor in series with said capacitor.

13. The system as claimed in claim 9, wherein said impedance unit further includes a second resistor in series with both said first resistor and said capacitor.

14. A system for monitoring the quality of an internal fluid in an electric power apparatus, said system comprising:
    a pulse input port for receiving a test pulse input signal from a pulse source;
    a test gap means for providing a test voltage across a test gap while said test gap means is immersed in the internal fluid within the electric power apparatus, said test gap means having an inherent capacitance; and
    a series impedance unit for providing an impedance in series with the inherent capacitance of said test gap means, said series impedance unit including a resistor in parallel with a capacitor, and said series impedance unit being coupled to said pulse input port and coupled to said test gap means.

15. A method of monitoring the dielectric properties of a fluid contained in an apparatus, said method comprising the steps of:
    providing a pulse charge through a restrictive impedance unit to a test gap that is immersed in the fluid, said restrictive impedance unit including a resistor in parallel with a capacitor;
    restricting the transfer of current to the test gap; and
    identifying whether the pulse charge has caused a breakdown of the fluid at the test gap.

16. The method as claimed in claim 15, wherein said apparatus is an electric power apparatus, and the fluid is oil.

17. The method as claimed in claim 16, wherein said method occurs while said electric power apparatus is operating.

* * * * *